United States Patent [19]

Vonderscher et al.

[11] Patent Number: 5,393,738

[45] Date of Patent: Feb. 28, 1995

[54] PHARMACEUTICAL COMPOSITIONS CONTAINING OCTREOTIDE AND EXCIPIENTS FOR ORAL OR RECTAL ADMINISTRATION

[75] Inventors: Jacky Vonderscher, Mulhouse; Joachim Franz, Riehen, Switzerland; Michel Steiger, Bern, Switzerland; Karl Hornung, Weil/Märkt, Switzerland

[73] Assignee: Sandoz, Ltd., Basel, Switzerland

[21] Appl. No.: 8,383

[22] Filed: Jan. 25, 1993

Related U.S. Application Data

[63] Continuation of Ser. No. 619,159, Nov. 28, 1990, abandoned, which is a continuation of Ser. No. 374,507, Jun. 19, 1989, abandoned, which is a continuation of Ser. No. 250,044, Sep. 19, 1988, abandoned, which is a continuation of Ser. No. 53,999, May 26, 1987, abandoned.

[30] Foreign Application Priority Data

May 27, 1986 [CH] Switzerland ............. 2138/86
May 27, 1986 [CH] Switzerland ............. 2144/86

[51] Int. Cl.$^6$ ............................................. A61K 37/24
[52] U.S. Cl. ........................................ 514/12; 530/399
[58] Field of Search ................... 514/12; 530/307, 399

[56] References Cited

U.S. PATENT DOCUMENTS

| | | | |
|---|---|---|---|
| 4,041,155 | 8/1977 | Fenichel et al. | 514/14 |
| 4,115,375 | 9/1978 | Pedersen | 530/854 |
| 4,151,276 | 4/1979 | Caulin et al. | 530/307 |
| 4,179,337 | 12/1979 | Davis et al. | 530/303 |
| 4,452,775 | 6/1984 | Kent | 514/12 |
| 4,457,916 | 7/1984 | Hayashi et al. | 424/101 X |
| 4,609,640 | 9/1986 | Morishita et al. | 514/12 |
| 4,613,500 | 9/1986 | Suzuki et al. | 514/12 X |
| 4,650,787 | 3/1987 | Schally et al. | 930/20 |
| 4,690,952 | 9/1987 | Kagatani et al. | 514/2 X |
| 4,900,730 | 2/1990 | Miyauchi | 514/12 |

FOREIGN PATENT DOCUMENTS

| | | |
|---|---|---|
| 56-122309 | 3/1981 | Japan . |
| 57-118509 | 7/1982 | Japan . |
| 57-146722 | 9/1982 | Japan . |
| 57-146723 | 9/1982 | Japan . |
| 2092002 | 8/1982 | United Kingdom . |
| 2127689 | 4/1984 | United Kingdom . |

OTHER PUBLICATIONS

Fuessl et al., "Oral absorption of the somatostahin . . . ", Clin. Sci., 72(2), pp. 255-257, 1987. CA 106(15):113817x.

Anria et al., "Pharmaceuticals containing calcitomin", CA 101(4):28293a.

Zofkova et al., Exp. Clin. Endocrinology 89(1), pp. 91-96, 1987, BIOSIS 87:294217.

Passariello et al., J. Clin. Endocrinol. Metab., 53(2), pp. 318-323, 1981, BISOS 82:142248.

Johannson, C. et al., Digestion 22(3), pp. 126-137 (1981); BIOSIS 82:181380.

Marco et al., J. Clin. Endovirol. Metab. 44(4), pp. 695-698 (1977), BIOSIS 77:197748.

Bruining et al., ACTA Endocrinol. Suppl., 113(279), pp. 334-339 (1986), BIOSIS 87:47750.

Primary Examiner—Michael G. Wityshyn
Assistant Examiner—C. Sayala
Attorney, Agent, or Firm—Robert S. Honor; Melvyn M. Kassenoff; Carl W. Battle

[57] ABSTRACT

Polypeptide compositions for inter alia SMS are provided containing a monosaccharide/sugar alcohol and/or a polyoxyalkylene ether having enhanced resorption properties for oral or rectal administration.

27 Claims, 3 Drawing Sheets

PHARMACEUTICAL COMPOSITIONS CONTAINING OCTREOTIDE AND EXCIPIENTS FOR ORAL OR RECTAL ADMINISTRATION

This is a continuation of application Ser. No. 07/619,159, filed Nov. 28, 1990, which in turn is a continuation of application Ser. No. 07/374,507, filed Jun. 30, 1989, which in turn is a continuation of application Ser. No. 07/250,044, filed Sep. 27, 1988, which in turn is a continuation of application Ser. No. 07/053,999, filed May 26, 1987, all of which are now abandoned.

This invention relates to pharmaceutical compositions containing polypeptide active agents, and adapted for gastrointestinal resorption, e.g. rectal administration and especially oral administration.

Medical treatment with polypeptides is often beset with problems. Polypeptides are generally quickly degraded to di-peptides and aminoacids in the body fluids and are usually badly resorbed through the gastro-intestinal wall, e.g. on oral and rectal administration. The low bioavailability often in the order of 0.1 to 1%, cannot generally be overcome by administering large doses because such administration leads to large intersubject variability in for example the area under the curve (AUC) or maximum drug concentration (Cpmax). Parenteral administration has thus to be selected to provide effective treatment. The usual way is by injection. Injectable pharmaceutical compositions are painful to administer and, when administration has to be repeated at regular intervals, treatment can become very painful for the patient.

Accordingly, the search for alternative polypeptide pharmaceutical compositions/on the one hand which are more acceptably tolerated and which can be more conveniently administered and on the other hand which provide a satisfactory bioavailability for an effective treatment/has been ongoing for many years. In the literature are numerous patent and academic publications describing new systems for improved gastro-intestinal absorption of polypeptides. Until now no system has proved to be of acceptable commercial utility for somatostatins, calcitonins and/or other polypeptides.

Figure 1:
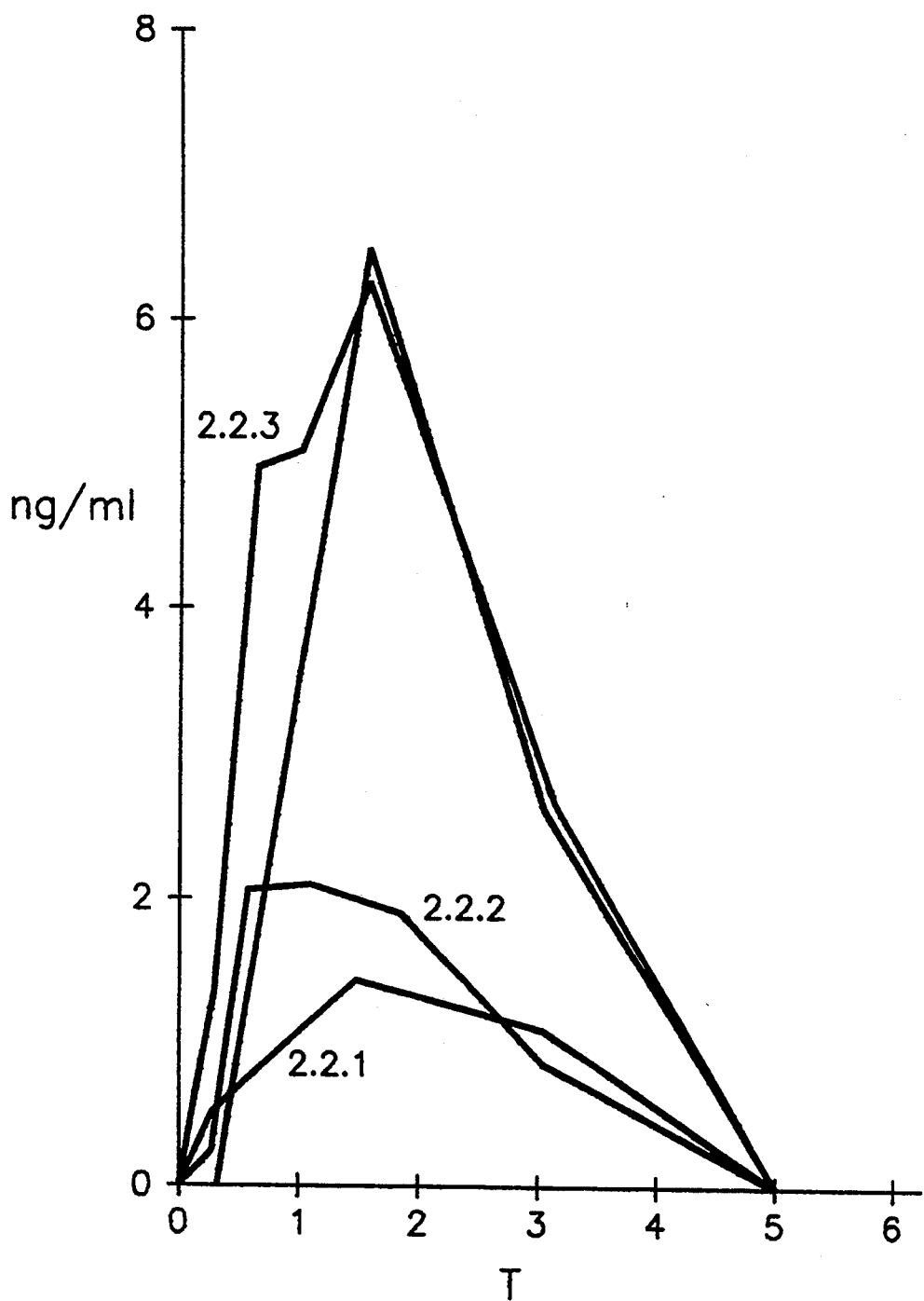
FIG. 1 shows the effect of polyoxyethylene cholestryl ethers on solid dosage forms.

After exhaustive testing we have found that monosaccharides or sugar alcohols and/or polyoxyalkylene ethers surprisingly provide an advantageous excipient base for pharmaceutical compositions adapted for gastro-intestinal resorption, e.g. rectal administration and preferably oral administration. Not only do they provide increased resorption of poly-peptides through the gut wall but also provide less intersubject variability in resorption parameters.

In one aspect the invention provides a pharmaceutical composition adapted for gastro-intestinal resorption comprising a polypeptide and having a relative bioavailability of drug in blood plasma of at least 160 per cent, on administration, compared with 100% for administration of the polypeptide alone.

The relative bioavailability may be greater than 300 per cent, or even more than 350 per cent, or more than 1000% as indicated in the following examples, compared with oral or rectal administration of the poly-peptide alone, e.g. based on administration of the poly-peptide in a conventional formulation.

Coefficients of variation (CV) as a means of determining intersubject variability in resorption are determined in conventional manner as a percentage, e.g. on the basis of the standard deviation in the mean AUC in ng.hr/ml divided by the mean AUC in ng.hr/ml or in similar manner on the basis of the Cpmax (ng/ml).

In humans and dogs bioavailability trials have shown that the CV may be in the order of 100%, for conventional compositions, e.g. aqueous solutions.

In another aspect the invention provides a pharmaceutical composition adapted for gastro-intestinal administration comprising a poly-peptide and having on administration a CV of less than 70 per cent.

Preferably at least 8 animals are used to determine the CV.

The bioavailability may be measured as the Area under the Curve over e.g. 3 or 7 hours, or up to 12 hours.

Controls for oral administration may comprise the same weight of poly-peptide in saline (0.9% w/w of sodium chloride). Controls for rectal administration may comprise the same weight of poly-peptide in a conventional suppository base, e.g. a triglyceride.

The pharmaceutical compositions according to the invention are preferably in unit dosage form.

Preferably they are suppositories for rectal administration. They may be made in conventional manner e.g, by moulding or compression procedures, The suppositories may be in the form of rectal capsules containing the pharmaceutical composition therein in solid or liquid form. If desired they may be of the hollow type, For oral administration the pharmaceutical composition according to the invention may be in the form of tablets, and preferably in the form of capsules.

The capsules may contain the poly-peptide in solid form, e.g. a powder, or, if the poly-peptide is sufficiently stable, in solution.

The pharmaceutical compositions according to the invention preferably are formulated such that on administration the poly-peptide is quickly brought into solution, e.g. in the gastric juices, for example more than 80% within 20 minutes, or released at a high concentration in the rectum or at the appropriate absorption site.

The pharmaceutical compositions according to the invention may contain excipients and enhancers which are, or equivalents of, the mono-saccharides/sugar alcohols and poly-oxyalkylene ethers described hereinafter. They may contain additionally conventional dispersing agents, e.g. colloidal silica, and diluents such as lactose.

Oral pharmaceutical compositions preferably are in the form of powders, preferably encapsulated. The powders are conveniently e.g.100 to 400 microns in diameter, e.g. around 200 microns.

As suppository base may be used cocoa butter. It is preferred to use synthetic or semi-synthetic suppository bases. These may be water insoluble fats, e.g. glycerides (mono-, di- and/or tri-) of fatty acids, e.g. made from coconut oil or palm kern oil.

Straight chain $C_{10}$–$C_{18}$ fatty acid glycerides, conveniently saturated, are preferred. Examples are Witepsol (Registered Trade Mark), e.g. Witepsol H series available from Dynamit Nobel, W. Germany; Suppocire (Registered Trade Mark), e.g. Suppocire AM or AS2, available from Gattefosse, France.

Other excipients may be present.

The bioavailability may be determined in conventional manner, e.g as follows:

Oral Bioavailability Method A (dogs)

The pharmaceutical composition according to the invention e.g. in the form of a capsule or a reference pharmaceutical composition containing the polypeptide,e.g. an aqueous solution, is administered to groups of 8 dogs (Beagle) of about 10 kg body weight which have been fasted for 20 hours.

After the pharmaceutical composition has been administered immediately thereafter 20 ml of isotonic aqueous sodium chloride solution (0.9% ) (hereinafter isotonic solution) are administered.

Blood samples from the vena saphena are obtained immediately before the administration of the pharmaceutical composition and 20 minutes, 40 minutes, 60 minutes, 90 minutes and 3,5 and 7 hours after the administration.

The blood is centrifuged and the poly-peptide concentration in the plasma ascertained in conventional manner using radioimmunoassay methods.

The relative bioavailability is determined on the basis of the area under the curve (AUC 0 to 7 hours).

Rectal Bioavailability Method B (Rabbits)

Suppositories (ca 1.5 g) made according to the invention, or conventional suppositories containing poly-peptide as controls, are administered rectally to rabbits (New Zealand Albino).

Blood samples from the ear vein are obtained immediately before administration of the suppository and 15 minutes, 30 minutes and 1,2,3,4,5,6 and 7 hours after application. The poly-peptide concentration is ascertained in the blood in conventional manner e.g. by radioimmunoassay methods.

The relative bioavailability is determined in analogous manner to method A.

Rectal Bioavailability Method C (Dogs)

This is effected in analogous manner to that described above, using, instead of rabbits, Beagle dogs.

Oral Bioavailability Method D (Rats)

Wistar rats-(about 300 g body weight) are fasted for 12 hours and anaesthetized with urethane (2 doses-of 0.7 mg/kg i.p.). The abdomen is opened to gain access to the gastrointestinal tract, in particular the jejunum. A solution of the pharmaceutical composition according to the invention or the poly-peptide as a control is injected into the gastro-intestinal tract, e.g. the jejunum.

Blood samples (e.g. 1 ml) are obtained 20 minutes, and 1, 2 and 3 hours after administration from the vena cava. The blood is centrifuged and the poly-peptide concentration in the plasma determined in conventional manner using a radioimmunoassay methods.

The relative bioavailability (Area under the curve over 3 hours) is determined in analogous manner to method A.

Oral Bioavailability Method E (Clinical trails)

The pharmaceutical compositions of the invention or control pharmaceutical compositions are administered to healthy volunteers in the morning. Blood samples are obtained over the next 12 hours and analysed by radioimmunoassay methods. The pharmaceutical compositions of the invention are especially useful for poly-peptides that are stable for long periods in gastric juices, e.g. those that show less than 50 per cent degradation within 2 hours in artificial gastric juices or during incubation with natural enzymes, e.g. α-chymotrypsin, collagenase, trypsin and pepsin, at 37° C.

A wide range of poly-peptides may be used in the pharmaceutical compositions of the invention. They may be peptide hormones or stable analogues thereof. Examples include somatostatins, calcitonins, ACE-inhibitors and renin inhibitors, and their analogues. The peptide may contain two or more amino acids, conveniently from 7 to 40,e.g. to 12 amino acids. They may e.g. be linear or be mono-cyclic.

Somatostatin itself is the compound of formula $$\text{H—Ala—Gly—Cys—Lys—Asn—Phe—Phe—Trp—Lys—Thr—Phe—Thr—Ser—Cys—OH}$$
$$\phantom{\text{H—Ala—}}1\phantom{\text{y—}}2\phantom{\text{—C}}3\phantom{\text{s—L}}4\phantom{\text{s—A}}5\phantom{\text{n—P}}6\phantom{\text{e—P}}7\phantom{\text{e—}}8\phantom{\text{p—L}}9\phantom{\text{s—T}}10\phantom{\text{—Ph}}11\phantom{\text{—T}}12\phantom{\text{r—S}}13\phantom{\text{r—C}}14$$

(with a disulfide bridge between Cys-3 and Cys-14)

By the term "analogue" as used herein is meant any of the known oligopeptides with somatostatin-like activity. The structure is derived from that of the naturally occurring tetradecapeptide somatostatin, which comprise at least one, different -amino acid residue in and/or fewer amino acid residue than, somatostain itself and which incorporate one or more partial peptide sequences occurring in the somatostatin molecule either intact or in derivatised form.

The preferred somatostatin analogues are those described in European patent No. 29 579 and U.S. Pat. No. 4,395,403, especially those specifically describe therein.

The preferred poly-peptide is octreotide. This has the formula $$\text{H—(D)Phe—Cys—Phe—(D)Trp—Lys—Thr—Cys—Thr-ol}$$

(with a disulfide bridge between the two Cys residues)

and is referred to hereinafter as SMS. Production of this compound is specifically described in the above patent.

A second group of somatostatin analogues are those described in Belgian Patent No. 892,315 (U.S. Pat. No. 4,435,385), especially examples 1 to 20 thereof, and preferably the compound of formula $$CH_3\text{—}(CH_2)_8\text{—CO—(D)Phe—Cys—Phe—(D)Trp—Lys—Thr—Cys—Thr-ol}$$

(with a disulfide bridge between the two Cys residues)

Further somatostain analogues are described in DE-Offenlegungsschrift 3,328,952, especially in examples 1 to 8 thereof.

Further somatostatin analogues are those of formula

1. $\text{H—Cys—Phe—Phe—(D)Trp—Lys—Thr—Phe—Cys—OH}$ (with a disulfide bridge between the two Cys residues)

[see Vale et al., Metabolism, 27, Supp. 1,139, (1978)]

2. 

Asn—Phe—Phe—(D)Trp—Lys—Thr—Phe—Gaba

[see European Patent Publication No. 1295 and Application No. 78 100 994.9].

3. 

MeAla—Tyr—(D)Trp—Lys—Val—Phe

[see Veber et al., Life Sciences, 34, 1371–1378 (1984) and European Patent Application No. 82106205.6 (published as No. 70 021)] also known as cyclo (N-Me-Ala-Tyr-D-Trp-Lys-Val-Phe).

4. 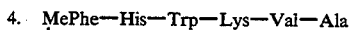

MePhe—His—Trp—Lys—Val—Ala

See R. F. Nutt et al. Klin. Wochenschr.(1986) 64 (Suppl. VII) 71–73.

The contents of all the above publications including the specific compounds are specifically incorporated herein by reference.

Unless stated otherwise, all amino acid radicals in the above formula according to usual nomenclature have the L-configuration configuration. -Thr-ol stands for the L-Threoninol- radical of formula

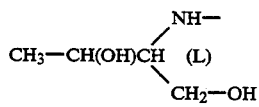

$$CH_3-CH(OH)CH \begin{matrix} NH- \\ \\ CH_2-OH \end{matrix} \text{(L)}$$

—MeAla— stands for the N-methyl-alanyl group.
—MePhe— stands for the N-methylphenylalanyl group.

Somatostatin and its analogues are useful for a wide variety of disorders associated with an increased secretion of growth hormone, e.g. for the treatment of diabetes mellitus, acromegaly etc. as well as gastro-intestinal disorders, e.g. stomach and intestinal bleeding, gastro-intestinal tumors. The poly-peptides are also useful against psoriasis, senile dementia and migraine.

Typical daily doses for parenteral injections are from 2 micrograms to 10 milligrams which may be administered 2 to 4 times a day in doses of from 0.5 micrograms to 5 mg, e.g. from about 50 to 200 micrograms, preferably subcutaneously.

Other poly-peptides include the calcitonins.

The calcitonins comprise a known class of pharmaceutically active, long-chain poly-peptides of varying, well documented pharmaceutical utility, e.g. salmon calcitonin (Salcatonin) human calcitonin and eel calcitonin (elcatonin). They lower calcium levels in the blood and are commonly employed in the treatment of e.g. Paget's disease, hypercalcaemia and osteoporosis. They may be naturally occurring and be prepared by extraction from natural sources or by synthesis (including By genetic engineering).

Alternatively they may only be prepared by synthesis. They may be analogues or derivative of natural products, e.g. in which one or more of the peptide residues present in the naturally occurring product is replaced, and/or in which the N- or C-terminal is modified, and/or the ring has been opened, Preferred is salmon calcitonin and open chain analogues thereof.

ACE-inhibitors and renin-inhibitors are known, e.g. ACE-inhibitors from Am. Med. J. 77,690. (1984), "Cardiovascular Pharmacology", M. Autonaccio, ed. 1984, page 119, in European Patent publications Nos. 158927 A, 156 455 A and in Ann. Rep. Med. Chem. 1985, Vol.20, Chapter 7. Renininhibitors are described in Ann. Rep. Med. Chem. 1985, Vol. 20, Chapter 26, in European Patent publications Nos. 156 321, 156 322, 165 151, 161 588 and 163 237. ACE-inhibitors and renin-inhibitors are mainly used against hypertension.

The polypeptides may be in free base form, in complex form or in pharmaceutically acceptable acid addition salt form. The complexes and salts are known and have the same order of activity and tolerability as the free base forms.

Suitable acid addition salts are e.g. the hydrochlorides and acetates. If desired the polypeptides may be used in the form of hydrates.

Little has been published on the biopharmaceutical properties of SMS. SMS is extremely stable in gastric juices. We have now found that SMS has an insignificant first pass effect. In the rat for example it is mainly excreted as the unchanged drug, about 80 per cent in the bile and 20 per cent in the urine. The main site of absorption is at the upper end of the intestinal tract i.e. the duodenum and jejunum. SMS bas thus a short transit time past the absorption site. We prefer to administer SMS orally in compositions which quickly release the SMS in the stomach and provide a high local concentration of SMS.

The present invention provides in another aspect a pharmaceutical composition adapted for improved gastro-intestinal resorption containing a) a mono-saccharide or sugar alcohol and/or b) a polyoxyalkylene ether.

Monosaccharides may be chosen from tetroses, pentoses, hexoses, heptoses, octoses and nonoses, especially erythrose, threose, arabinose, lyxose, xylose, ribose, rhamnose, fuxose, digitalose, quinovose, apiose, glucose, mannose, galaktose, fructose, sorbose, gulose, talose, allose, altrose, idose and glucoheptulose. Deoxy compounds like 3-deoxyglycose, amino compounds like glucosamine, ether compounds like 3-0-methylglucose and 3-0-butylglucose may also be used.

As mono-saccharide is preferably used glucose, fructose, or xylose, especially glucose and most especially xylose.

Sugar alcohols are preferably reduced forms of mono-saccharides. Preferred examples are mannitol and sorbitol, preferably mannitol.

Especially preferred components are polyoxyalkylene higher alcohol ethers, e,g. of the general formula (A)

$$RO\text{-}\!\!\left[(CH_2)_n\text{—}O\right]_{\overline{x}}H \qquad (A)$$

wherein RO is the residue of a higher alcohol especially a higher alkanol or alkylphenol, such as lauryl or cetyl alcohol, or a sterol residue, especially a lanosterol, dihydrocholesterol or cholesterol residue, as well as mixtures of two or more such ethers.

Preferred polyoxyalkylene ethers fop use in accordance with the invention are polyoxyethylene and polyoxypropylene ethers (i.e. wherein in the formula above is 2 or 3) in particular polyoxyethylene and polyoxyethylene lauryl, cetyl and cholesteryl ethers as well as mixtures of two or more such ethers; more preferably the polyoxyalkylene ether is a polyoxyethylene ether of average 24 repeating units.

The hydroxy group at the end alkylene unit of such ethers as aforesaid may be partially or completely acylated, by e.g. acyl residues of aliphatic carboxylic acids, such as acetic acid.

Preferred ethers for use in accordance with the invention have a hydrophilic-lipophilic balance (HLB group number) of from about 10 to about 20, especially from about 12 to about 16.

Especially suitable ethers for use in accordance with the invention are those wherein the average number of repeating units in the polyoxyalkylene moiety (x in the formula above) is from 4 to 75, suitably 8 to 30, more especially 16 to 26. The ethers may be obtained in accordance with known techniques. A wide variety of such products are commercially available and e.g. offered for sale e.g. by the company Amerchol under the trade-name Solulan ®, the companies KAO Soap, ICI and Atlas under the trade-names Emalex ®, Brij ® Laureth ® and from the company Croda under the trade-name, Cetomacrogol ®.

Examples of polyoxyalkylene ethers suitable for use in accordance with the invention are as follows:
(POE=polyoxyethylene ether; POP=polyoxypropylene ether; x=average No. of repeating units in the POP/POE moiety).

1. Cholesteryl ethers:
   1.1 Solulan ® C-24 - POE, x=24.
2. Ethers of Lanolin alcohols:
   2.1 Solulan ® 16 - POE, x=16.
   2.2 Solulan ® 25 - POE, x=25.
   2.3 Solulan ® 75 - POE, x=75.
   2.4 Solulan ® PB-10 - PPE, x=10.
   2.5 Solulan ® 98 - POE, x=10 - partially acetylated.
   2.6 Solulan ® 97 - POE, x=9 - fully acetylated.
3. Lauryl ethers:
   3.1 Emalex ® 709/Laureth ® 9 - POE, x=9.
   3.2 Laureth ® 4/ Brij ® 30 - POE, x=4.
   3.3 Laureth ® 23/ Brij ® 35 - POE, x=23.
4. Cetyl ethers:
   4.1 Cetomacrogol ® - POE, x=20 to 24.

Lanolin alcohols are also known as wool fat alcohols and are a mixture of cholesterol, di hydrochol esterol and lanosterol.

Preferred ethers for use in accordance with the present invention are polyoxyethylene cholesteryl ethers, i.e. of the above formula A, wherein n=2 and RO is a cholesterol residue, especially such ethers wherein the number of repeating units in the polyoxyethylene moiety is from 16 to 26, most preferably about 24.

More preferably such ethers are substantially free from contaminents in particular from other polyoxyalkylene ethers. Most preferably they comprise at least 75%, more preferably at least 85%, and most preferably at least 90% by weight of pure polyoxyethylene cholesteryl ether.

The pharmaceutical compositions of the invention may be used for the same indications as for other forms of the same active agent, e.g, parenteral forms.

The dosages of active agent, mono-saccharide or sugar alcohol and polyoxyalkylene ether may be ascertained by conventional bioavailability testing, e.g. by the methods described above in animals or clinically. If desired the testing may be effected for repeated applications, e.g. in the steady state and incorporate food interaction studies. Concentrations of active agents in the blood may be measured in conventional manner, e.g. by radio-immunoassay methods.

The pharmaceutical compositions of the invention are conveniently administered 2 to 4 times a day, conveniently when the subject is in a fasting state, e.g. about an hour before mealtime.

The exact amount of component a), mono-saccharide or sugar alcohol, may vary between wide limits. Conveniently they are present in a dose of from 10 to 500 mg per unit dosage form, preferably about 50 to 100 mg per unit dosage form.

The exact amount of component b), polyoxyalkylene ether, may vary between wide limits. It is preferred to have preferably between 5 and 200 mg per unit dosage form. For oral dosage forms the amount of polyoxyalkylene ether is preferably from about 20 to 200 mg. For rectal application the amount of polyoxyalkylene ether is preferably about 40 to 60 mg.

When both component a) mono-saccharide/sugar alcohol and b) polyoxyalkylene ether are present, preferably about 10 to 500 mg component a), e.g. about 400 mg, are present for a solid dosage form or from 10 mg to 10 g per 20 ml in the case of a liquid form.

Preferably about 5 to 200 mg, e.g. about 100 mg polyalkylene ether per, e.g. solid, dosage form is present or in the case of a liquid about 5 to 500 mg polyalkylene ether per 20 ml.

The exact limit of polypeptide present may also vary between wide limits.

Conveniently the amount is in the range from about 2 mg to 10 mg. For SMS the amount is preferably from 100 microgram to 35 mg per unit dosage form, e.g. from 2 to 8 mg.

The combination of xylose and polyoxyethylene ether has been found to provide a particularly interesting excipient base for pharmaceutical compositions, e.g. importing a low coefficient of variation.

In another aspect the present invention provides a composition comprising xylose and a polyoxyethylene ether preferably in a weight ratio of from 2:1 to 1:2. Preferably from 50 to 100 mg of polyoxyethylene ether is present per unit dosage form. These compositions may be worked up as pharmaceutical compositions in analogous manner to that described herein or in the literature.

Whilst we are not willing to be bound in any way, it is believed that loose adducts are formed between pharmacologically active agents such as SMS and mono-saccharides and sugar alcohols and polyoxyalkylene ethers which lead to an increased resorption.

As indicated above the pharmaceutical composition of the invention may be made in conventional manner by mixing the poly-peptide mono-saccharide/sugar alcohol and polyoxyethylene ether.

In the following examples:
AUC=(Area under the Curve) refers to mean values (unless otherwise stated) in ng.hr/ml. They refer to 0 to 7 hours after administration unless otherwise stated.
Cpmax values are ng/ml (unless otherwise stated).
SEM=Standard error in the mean
n=number of animals
CV=coefficient of variation
Relative and absolute bioavailability are given as per cent of reference values.
SMS ac=SMS acetate
2.3 mg SMS acetate is equivalent to 2 mg pure SMS.
5.8 mg SMS acetate is equivalent to 5 mg pure SMS.
POECE=Polyoxyethylene cholesterol ether.

POECE (A) contains asteroid component at least 92 per cent by weight of cholesterol and an average number of 24 repeating units of oxyethylene.

POECE (B) contains about 60% polyoxyethylene steroid ethers, the major component being cholesterol and with an average number of 24 repeating units of oxyethylene. The remainder is in a similarly ethoxylated higher alcohol, mainly hexyldecanol.

It is available from Amerchol, Edison, N.J., USA Saline (0.9% NaCl) comprises bidistilled water.

Further details of supplies and specifications e.g. of Solulan C24, are given in H. P. Fiedler, Lexikon der Hilfsstoffe, 2nd Edition, Edito Cantor, Aulendorf.

The figures show plasma levels (ng/ml) versus time (T) in hours.

EXAMPLES

1. Bioavailability of SMS from Suppositories 1.1 For Method B (see above), suppositories (1.5 g) moulded or compressed) are made from triglyceride (Witepsol)$^R$ containing 5.8 mg SMS as acetate (=5 mg SMS). As control served an i.v. injection (0.58 mg SMS-acetate) to determine absolute bioavailability.

|  | AUC ± S.E.M. | Abs. Bioavailability [%] |
| --- | --- | --- |
| Suppo with SMS ac alone (moulded) | 968 ± 219 | 22 (n = 6) |
| Suppo with POECE (A) (50 mg) and Mannitol (90 mg) compressed | 1617 ± 366 | 37 (n = 6) |
| Suppo with POECE (A) (50 mg) and Mannitol (90 mg) moulded | 2263 ± 504 | 55 (n = 6) |

On rectal administration the relative bioavailability is over 160 per cent of the reference for the composition of the invention.

1.2 Suppositories with the same doses as in example 1.1

| Results | | |
| --- | --- | --- |
|  | AUC ± S.E.M. | Abs. Bioavailability [%] |
| Suppo with SMS ac alone (hollow type) | 2 ± 3 | 1 (n = 3) |
| Suppo with POECE (A) (50 mg) and Mannitol (40 mg) (hollow type) | 64 ± 14 | 28 (n = 4) |

On rectal administration the relative bioavailability is increased to over 1000%.

EXAMPLES

2. Bioavailability of SMS on oral administration

Method A (see above) was effected over 7 hours. Amounts of SMS below refer to SMS ac.

| 2.1 Effect of a solid form in comparison with an aqueous solution | | | |
| --- | --- | --- | --- |
| Composition | n | AUC ± S.E.M. | Relative Bioavailability [%] |
| 2.3 mg SMS in 20 ml isoton. solution (NaCl 0.9% in dist. water) [Reference] | 4 | 6.6 ± 1.1 | 100 |
| 2.3 mg SMS +100 mg Lactose | 4 | 6.5 ± 1.8 | 100 |

Analysis limit of RIA-Method: 0.25 ng/ml

| 2.2 Effect of POECE on solid dosage forms | | | |
| --- | --- | --- | --- |
| Composition | n | AUC ± S.E.M. | Relative Bioavailability [%] |
| 2.2.1 2.3 mg SMS +100 mg Lactose | 8 | 4.3 ± 0.9 | 100 |
| 2.2.2 2.3 mg SMS +10 mg POECE (B) | 4 | 5.2 ± 1.9 | 121 |
| 2.2.3 2.3 mg SMS +20 mg POECE (B) | 4 | 16.3 ± 5.2 | 379 |
| 2.2.4 2.3 mg SMS +50 mg POECE (B) | 8 | 14.0 ± 3.3 | 326 |
| 2.2.5 2.3 mg SMS +100 mg POECE (B) | 8 | 13.8 ± 3.0 | 321 |

[Analysis limit of RIA-Method: 1 ng/ml]

As indicated the oral relative bioavailability is increased to over 120%, even over 300% by increasing the POECE: SMS ratio to above 8:1.

The plasma curves of trials 2.2.1, 2.2.2, 2.2.3 and 2.2.5 are shown in FIG. 1.

| 2.3 Effects of glucose in aqueous solutions | | | |
| --- | --- | --- | --- |
| Composition | n | AUC ± S.E.M. | Relative Bioavail. [%] |
| 2.1.1 Reference | 4 | 6.6 ± 1.1 | 100 |
| 2.3.1 2.3 mg SMS in 20 ml glucose-solution (10 g glucose/20 ml dist. water | 4 | 19.9 ± 1.4 | 302 |

[Analysis limit of RIA-Method: 0.25 ng/ml)

Figure 2:
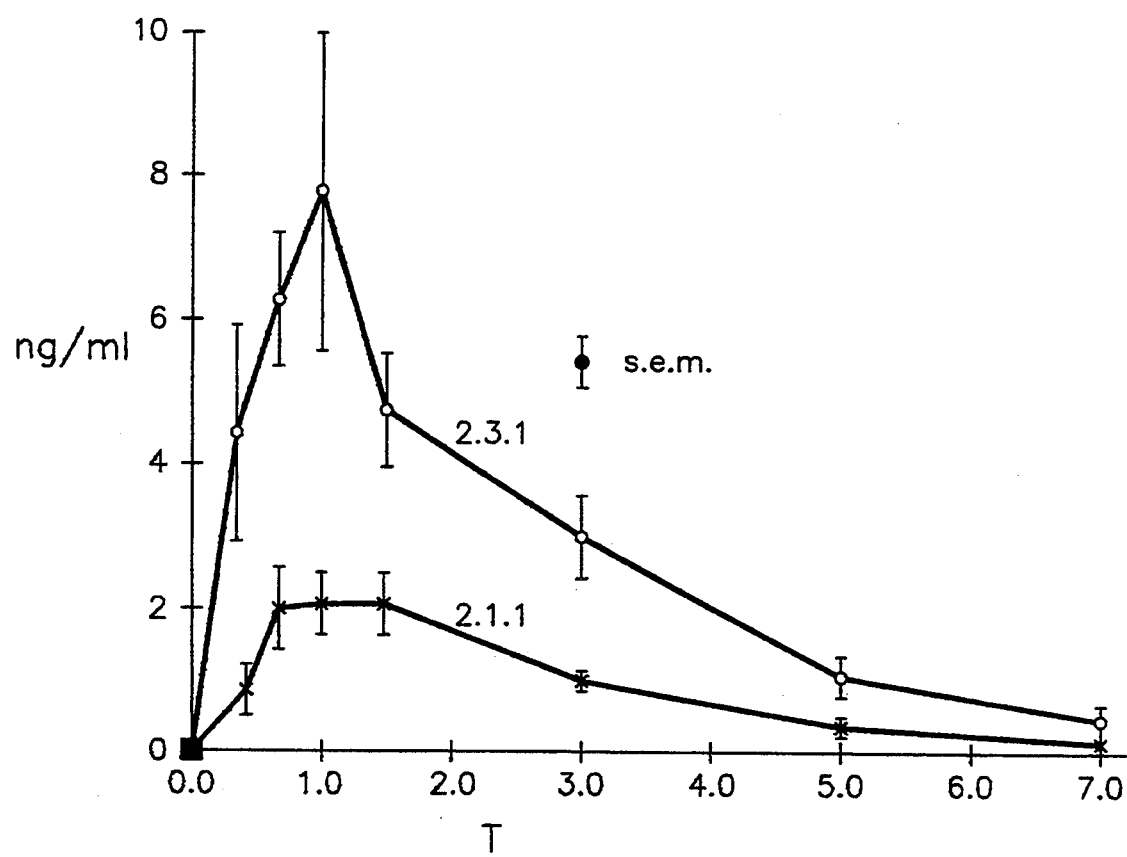
FIG. 2 shows the effects of glucose in aqueous solutions.

The plasma curves of trials 2.1.1 and 2.3.1 are given in FIG. 2.

| 2.4 Effects of glucose in hard gelatine capsules | | | |
| --- | --- | --- | --- |
| 2.2.1 Reference | 8 | 4.3 ± 0.9 | 100 |
| 2.4.1 2.3 mg SMS +400 mg Glucose | 4 | 13.1 ± 7.1 | 305 |

[Analysis limit of RIA-Method: 1 ng/ml]

| 2.5 Effect of combination of glucose with POECE (B) in hard gelatine capsules | | | |
| --- | --- | --- | --- |
| Composition | n | AUC ± S.E.M. | Relative Bioavailability [%] |
| 2.2.1 Reference (2.3 mg SMS) | 8 | 4.3 ± 0.9 | 100 |
| 2.2.5 +100 mg POECE (B) (2.3. mg SMS) | 8 | 13.8 ± 3.0 | 321 |
| 2.4.1 +400 mg Glucose (2.3 mg SMS) | 4 | 13.1 ± 7.1 | 305 |
| 2.5.1 2.3 mg SMS +100 mg POECE (B) | 4 | 48.8 ± 17.9 | 1135 |

2.5 Effect of combination of glucose with POECE (B) in hard gelatine capsules

| Composition | n | AUC ± S.E.M. | Relative Bioavailability [%] |
|---|---|---|---|
| +400 mg Glucose | | | |

[Analysis limit of RIA-Method: 1 ng/ml]

Figure 3:
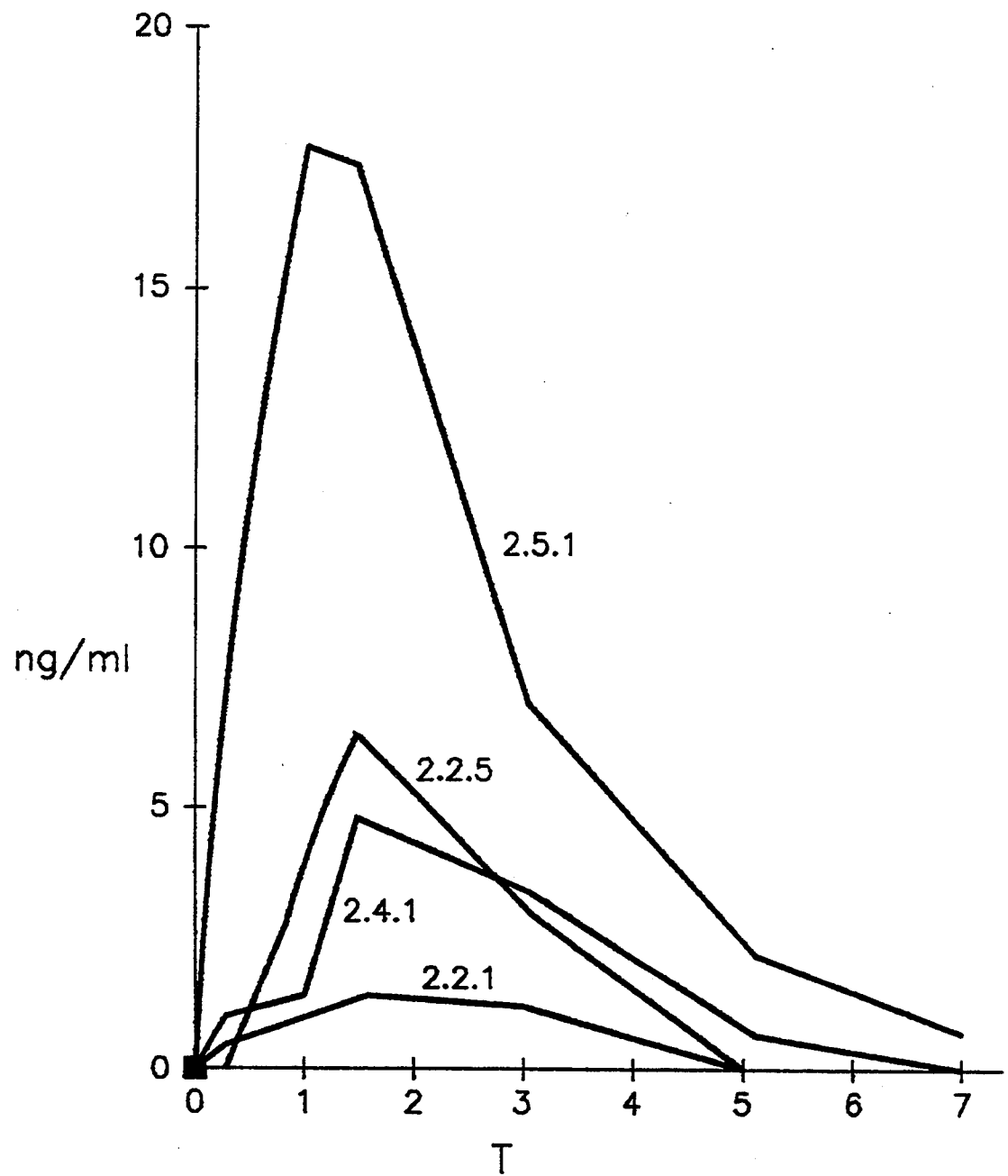
FIG. 3 shows the effects of the combination of glucose with polyoxyethylene cholestryl ethers in hard gelatin capsules.

The plasma curves of trials 2.2.1, 2.2.5, 2.4.1 and 2.5.1 are shown in FIG. 3.

The synergystic effect of the combination of POECE (B) with glucose is clearly shown.

3. Determination of SMS bioavailability locally applied in jejunum

Method D (see above). Bioavailablity (AUC) is determined over 3 hours. Amounts of SMS below refer to SMS ac.

3.1 Effect of POECE

| Composition | n | AUC + S.E.M. | Relative Bioavailability |
|---|---|---|---|
| 3.1.1 50 Microgram SMS in 0.5 ml isotonic aqueous solution (NaCl 0.9%) [Reference] | 9 | 2.0 ± 1.2 | 100% |
| 3.1.2 As for 3.1.1 with + 7.2 mg POECE (B) | 6 | 125.4 ± 42.3 | 6270% |

3.2 Effect of glucose and xylose in aqueous solutions

| Composition | n | AUC (0–3 h) + SEM | Relative Bioavail. |
|---|---|---|---|
| 3.2.1 50 Microgram SMS in 0.5 ml isotonic aqueous solution (NaCl 0.9%) [Reference]* | 6 | 0.5 ± 0.4 | 100% |
| 3.2.2 50 Microgram SMS +27.5 mg Glucose in 0.5 ml twice distilled water* | 6 | 3.8 ± 0.6 | 760% |
| 3.2.3 50 Microgram SMS +100 mg Glucose in 0.5 ml twice distilled water** | 6 | 2.6 ± 0.4 | 520% |
| 3.2.4 50 Microgram SMS +250 mg Glucose in 0.5 ml twice distilled water** | 6 | 26.2 ± 7.2 | 5240% |
| 3.2.5 50 Microgram SMS +23 mg Xylose in 0.5 ml twice distilled water* | 6 | 6.6 ± 2.0 | 1320% |
| 3.2.6 50 Microgram SMS +85 mg Xylose in 0.5 ml twice distilled water** | 6 | 6.1 ± 0.6 | 1220 |
| 3.2.7 50 Microgram SMS +210 mg Xylose in 0.5 ml twice distilled water** | 6 | 46.2 ± 7.8 | 9240 |

[Analysis limit of RIA-Method: 0.2 mg/ml]
With equivalent amounts of mono-saccharide the resorption increase with xylose is better than with glucose.
*isotonic
**hypertonic

EXAMPLE 4

Coefficient of variation

Method: Oral bioavailability method A 2.3 mg SMS as acetate, 100 mg POECE (A) and 100 mg xylose in a hard gelatine capsule (Composition A) and a control of 2.3 mg SMS ac in 20 ml saline (Reference) are administrered to groups of 8 beagle dogs. The experiment was repeated.

Results obtained (AUC, means, median and Cpmax mean, median and coefficient of variation) are shown in the following table:

| Composition | AUC Mean | AUC Median | CV % | Cpmax Mean | Cpmax Median | CV % |
|---|---|---|---|---|---|---|
| 4.1.1 Reference [1st administration] | 24.8 | 12.5 | 112 | 6.8 | 3.8 | 100 |
| 4.1.2 Reference [2nd administration] | 25.4 | 14.3 | 112 | 6.5 | 4.3 | 98 |
| 4.2.1 Composition A [1st administration] | 48.2 | 46.8 | 49 | 21.7 | 25.3 | 38 |
| 4.2.2 Composition A [2nd administration] | 39.6 | 34.7 | 46 | 14.9 | 13.5 | 41 |

Based on the AUC and Cpmax median values there is a significant reduction of intersubject coefficient of variation with the compositions of the invention. Additionally, the AUC and Cpmax mean values are closer to the median values.

Additionally, the coefficient of variation values are similar from one trial to the other. This indicates that the intrasubject variability is small.

For the pharmaceutical composition of the invention the AUC median values are increased by a factor of 2–3 over the control value and the Cpmax median value is increased by a factor of at least 3.

EXAMPLE 5

Coeffeicient of Variation

Effects of different doses of POECE in solution or as a powder

Bioavailability Method A

Solutions and powders containing 2.3 mg SMS as acetate are administered to beagle dogs in accordance with bioavailability method A and in analogous manner to Example 4.

Results are shown on the following table (wherein POECE is POECE B and HGC stands for hard gelatine capsule).

| COMPOSITION (2.3 mg SMS +) | AUC Mean | AUC Median | CV % | Cpmax Mean | Cpmax Median | CV % |
|---|---|---|---|---|---|---|
| 5.1.1 Reference in 20 ml saline | 15.79 | 9.60 | 86.85 | 4.54 | 3.98 | 73.69 |
| 5.1.2 100 mg POECE in 20 ml saline | 46.38 | 44.60 | 38.43 | 30.47 | 24.47 | 60.69 |
| 5.1.3 100 mg Xylose in 20 ml saline | 15.85 | 11.15 | 67.48 | 5.47 | 5.14 | 51.71 |
| 5.2.1 100 mg POECE + 100 mg Xylose (HGC) | 54.12 | 49.82 | 25.50 | 33.80 | 33.00 | 53.85 |

The results show that in solution there is a decrease in coefficient of variation (compare 5.1.2; 5.1.3; with the reference 5.1.1). Simultaneously the median values of AUC and Cpmax show an increase.

In solid dosage forms increases in AUC values and Cpmax values are observed (compare 5.2.1; 5.2.2 with 5.1.1).

EXAMPLE 6

In analogous manner to that in example 1, the following results have been obtained using 5.8 mg SMS acetate. Different types of suppository are used, e.g. hollow, moulded or compressed type.

|  |  | n | AUC | T max hr. | Bioavailability % |
|---|---|---|---|---|---|
| 6.1.1 | Reference (i.v.) 0.58 mg SMS as acetate | 6 | 4128 ± 522 | 0.14 | 100 |
| 6.1.2 | Hollow type with 50 mg POECE (A) +50 mg Glucose | 12 | 2406 ± 394 | 0.83 | 58 |
| 6.1.3 | Moulded type with 50 mg POECE (A) | 6 | 2263 ± 504 | 1.08 | 55 |
| 6.1.4 | As for 6.1.2 in form of capsule containing 100 mg glucose | 6 | 2269 ± 599 | 0.75 | 55 |

EXAMPLE 7

In analogous manner to that described under 1.1 2.3 mg SMS acetate were administered instead of 5.8 mg either in the form of rectal capsules or compressed suppositories. Results obtained are:

|  | Composition | n | Bioavailability* % |
|---|---|---|---|
| 7.1 | Capsule type 96 mg Xylose + POECE (B) | 6 | 59 |
| 7.2 | Compressed type as for 7.1 | 5 | 52.5 |
| 7.3 | Compressed type containing Mannitol 96 mg | 6 | 2.0 |
| 7.4 | As for 7.3 with additionally 50 mg POECE (B) | 6 | 17.7 |
| 7.5 | Capsule type with Xylose 96 mg | 6 | 3.8 |
| 7.6 | Capsule type with Lactose | 6 | 2.4 |

|  | Composition | n | Bioavailability* % |
|---|---|---|---|
| 7.7 | 200 mg Capsule type with Lactose 200 mg and POECE (B) 50 mg | 6 | 45.7 |

*compared to i.v. injection

Preparation of formulations

Hard gelatine capsules

A hard gelatine capsule contains:

| Ingredient | Weight |
|---|---|
| SMS as acetate | 2,3 mg* |
| POECE (A) | 100 mg |
| Xylose | 100 mg |
| Colloidal silica+ | 2.5–3.3 mg |

*equivalent to 2 mg SMS.
+Brand Aerosil 200.

The components are mixed together using an excess of 5 per cent SMS to compensate for losses in production, sieved through 200 micron holes, and filled into hard gelatine capsules.

Dissolution rate (Rotating Paddle method 0.1 NHCl) at least 85.5 per cent after 20 minutes.

The above is the preferred formulation. Pharmaceutical compositions of the invention containing other amounts of ingredients and other ingredients may be made in analogous manner, e.g. containing the equivalent of 8 mg SMS, 100 mg POECE (A) and 100 mg xylose.

Other formulations are made in conventional manner.

The above formulations may be modified by including an equivalent amount of salmon calcitonin in place of SMS.

Suppositories

A suppository contains, e.g.

| Ingredient | Weight |
|---|---|
| 1. SMS as acetate | 5.8 mg* |
| 2. Crystalline citric acid | 0.85 mg |
| 3. Trisodium citradea dihydrate | 0.5 mg |
| 4. Mannitol | 92.85 mg |
| 5. POECE (B) | 50 mg |
| 6. Stearic acid | 3 mg |
| 7. Magnesium stearate | 0.7 mg |
| 8. Suppository base to ca (e.g. Witespol H15) | 1.5 to 1.9 g* |

*corresponding to 5 mg SMS

Ingredients 1 to 4 and Ingredients 5 to 7 are mixed separately and then combined to give a powder filing. If desired the ingredients can be granulated.

The powder or granulate is then mixed with molten suppository base, poured into suppository moulds and cooled.

If desired the ingredients are mixed (omitting totally stearic acid and magnesium stearate) and then mixed with powdered suppository base and compressed at low temperatures, e.g. $-10°$ C. into suppository shapes, or moulded at slightly elevated temperatures.

Suppositories containing 0.5 and 1 mg SMS may be made in analogous manner. If desired the POECE B may be Cetomacrogol 1000.

EXAMPLE 8

Clinical trials

Clinical trials were effected with an aqueous solution containing 8 mg SMS (composition A) and a hard gelatine capsule containing 2 mg SMS, 100 mg xylose and 100 mg POECE (B) (composition B).

The compositions were administered in the morning and blood samples taken over the next 12 hours. The AUC was calculated over the next 12 hours.

Results (adjusted to a single dose of 8 mg) are as follows:

| Composition | AUC (Median) | CV (%) | Cpmax (median) | CV % |
|---|---|---|---|---|
| A | 1.24 | 128 | 0.32 | 132 |
| B | 31.29 | 71 | 8.72 | 66 |

The results shown that the pharmaceutical composition of the invention has a significantly lower coefficient of variation than the aqueous solution and a significantly increased bioavailability.

The Cpmax of composition B is well over the Cpmax of about 3.2 ng ml$^{-1}$ obtained on administration s.c. of a therapeutic dose of 100 micrograms of SMS.

What we claim is:

1. A pharmaceutical composition comprising octreotide and an excipient selected from the group consisting of a) a, monosaccharide, b) a sugar alcohol, c) a monosaccharide and a polyoxyalkylene ether, and d) a sugar alcohol and a polyoxyalkylene ether, and said composition being adapted for gastro-intestinal resorption by oral or rectal administration.

2. A pharmaceutical composition according to claim 1 wherein said excipient c) comprises xylose and polyoxyethylene ether.

3. A pharmaceutical composition according to claim 2 wherein the ratio of xylose to ether is from 2:1 to 1:2.

4. A pharmaceutical composition according to claim 1, wherein the monosaccharide is glucose.

5. A pharmaceutical composition according to claim 1 wherein the monosaccharide is xylose.

6. A pharmaceutical composition according to claim 1 in solid unit dosage form.

7. A pharmaceutical composition according to claim 6 containing from 10 to 500 mg of said monosaccharide or sugar alcohol.

8. A pharmaceutical composition according to claim 6 containing from 5 to 200 mg of said polyoxyalkylene ether.

9. A pharmaceutical composition according to claim 8 wherein the polyoxyalkylene ether is a polyoxyethylene ether.

10. A pharmaceutical composition according to claim 8 wherein the polyoxyalkylene ether is a polyoxyethylene ether of average 24 repeating units.

11. A pharmaceutical composition according to claim 10 wherein the ether is a steroid ether.

12. A pharmaceutical composition according to claim 11 wherein the ether is a polyoxyethylene cholesteryl ether.

13. A pharmaceutical composition according to claim 12 containing 100 mg polyoxyethylene cholesteryl ether, 100 mg xylose and octreotide.

14. A pharmaceutical composition comprising octreotide and an excipient selected from the group consisting of a) a monosaccharide, b) a sugar alcohol, c) a monosaccharide and a polyoxyalkylene ether, and d) a sugar alcohol and a polyoxyalkylene ether, and said composition being adapted for gastro-intestinal resorption by oral or rectal administration and having a relative bioavailability of said octreotide, in blood plasma up to 12 hours after administration, of at least 160% by oral or rectal administration compared with 100% by oral or rectal administration of said octreotide alone.

15. A pharmaceutical composition according to claim 14 containing in a unit dosage form from 50 to 100 mg of said monosaccharide or sugar alcohol.

16. A pharmaceutical composition according to claim 15 wherein said polyoxyalkylene ether is a polyoxyethylene ether.

17. A pharmaceutical composition according to claim 15 wherein said polyoxyalkylene ether is a polyoxyethylene ether of average 24 repeating units.

18. A pharmaceutical composition according to claim 17 wherein said ether is a steroid.

19. A pharmaceutical composition according to claim 18 wherein said ether is a polyoxyethylene cholesteryl ether.

20. A pharmaceutical suppository composition comprising octreotide, a polyoxyalkylene ether excipient, and a suppository base, and said composition being adapted for gastro-intestinal resorption by rectal administration.

21. A pharmaceutical suppository composition according to claim 20 additionally comprising a monosaccharide or sugar alcohol.

22. A pharmaceutical suppository composition according to claim 20 containing in a unit dosage form from 5 to 200 mg of said polyoxyalkylene ether.

23. A pharmaceutical suppository composition according to claim 22 additionally comprising a monosaccharide or sugar alcohol.

24. A pharmaceutical suppository composition according to claim 22 wherein said polyoxyalkylene ether is a polyoxyethylene ether.

25. A pharmaceutical suppository composition according to claim 22 wherein said polyoxyalkylene ether is a polyoxyethylene ether of average 24 repeating units.

26. A pharmaceutical suppository composition according to claim 25 wherein said ether is a steroid ether.

27. A pharmaceutical suppository composition according to claim 26 wherein said ether is a polyoxyethylene cholesteryl ether.

* * * * *